US012599373B2

(12) United States Patent
Van Liere et al.

(10) Patent No.: US 12,599,373 B2
(45) **Date of Patent: *Apr. 14, 2026**

(54) BIOPSY DEVICE HAVING A LINEAR MOTOR

(71) Applicant: C. R. Bard, Inc., Franklin Lakes, NJ (US)

(72) Inventors: Chad Van Liere, Phoenix, AZ (US); Aseem Singh, Tempe, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 1030 days.

This patent is subject to a terminal disclaimer.

(21) Appl. No.: 17/724,961

(22) Filed: Apr. 20, 2022

(65) Prior Publication Data

US 2022/0240906 A1     Aug. 4, 2022

Related U.S. Application Data

(63) Continuation of application No. 16/761,519, filed as application No. PCT/US2017/067543 on Dec. 20, 2017, now Pat. No. 11,337,682.

(51) Int. Cl.
*A61B 10/02*          (2006.01)

(52) U.S. Cl.
CPC ........ *A61B 10/0266* (2013.01); *A61B 10/025* (2013.01); *A61B 2010/0208* (2013.01); *A61B 2010/0258* (2013.01)

(58) Field of Classification Search
CPC ............ A61B 10/0291; A61B 10/0283; A61B 10/0045; A61B 10/02; A61B 2010/009; A61B 2010/0216
See application file for complete search history.

(56) References Cited

U.S. PATENT DOCUMENTS

| | | | |
|---|---|---|---|
| 5,557,154 A * | 9/1996 | Erhart ................. | F16H 25/2252 |
| | | | 417/415 |
| 5,653,713 A | 8/1997 | Michelson | |
| 6,617,760 B1 | 9/2003 | Peterson et al. | |
| 6,758,824 B1 | 7/2004 | Miller et al. | |

(Continued)

FOREIGN PATENT DOCUMENTS

| | | |
|---|---|---|
| EP | 2889015 A1 | 7/2015 |
| WO | 2015061643 A3 | 4/2015 |

*Primary Examiner* — Sean P Dougherty
(74) *Attorney, Agent, or Firm* — Dinsmore & Shohl LLP

(57) ABSTRACT

A biopsy device includes a device housing, a linear motor, and a controller circuit. The controller circuit has a processor circuit, a first feedback circuit, and a second feedback circuit. The first feedback circuit and the second feedback circuit operate simultaneously. The processor circuit executes program instructions to control an axial advancement of the distal end of the linear motor shaft in accordance with a linear motor shaft advancement profile based on first control signals received from at least one drive characteristic sensor of the first feedback circuit, and executes program instructions to keep the distal end of the linear motor shaft at a constant axial position, as offset by the position indicated by the linear motor shaft advancement profile, based on second control signals received from the housing position detector of the second feedback circuit so as to compensate for user movement of the device housing.

20 Claims, 4 Drawing Sheets

(56) References Cited

U.S. PATENT DOCUMENTS

| | | | |
|---|---|---|---|
| 6,846,314 B2 | 1/2005 | Shapira | |
| 7,670,328 B2 | 3/2010 | Miller | |
| 7,815,642 B2 | 10/2010 | Miller | |
| 7,883,476 B2 | 2/2011 | Miller et al. | |
| 8,043,229 B2 | 10/2011 | Mulvihill et al. | |
| 8,109,886 B2 | 2/2012 | Miller et al. | |
| 8,277,393 B2 | 10/2012 | Miler et al. | |
| 8,328,738 B2 | 12/2012 | Frankhouser et al. | |
| 8,591,435 B2 * | 11/2013 | Ritchart | A61B 10/0266 |
| | | | 600/568 |
| 8,690,791 B2 | 4/2014 | Miller | |
| 8,777,871 B2 | 7/2014 | Frankhouser et al. | |
| 8,777,944 B2 | 7/2014 | Frankhouser et al. | |
| 8,821,493 B2 | 9/2014 | Anderson | |
| 8,864,687 B2 | 10/2014 | May et al. | |
| 8,870,865 B2 | 10/2014 | Frankhouser et al. | |
| 8,876,826 B2 | 11/2014 | Miller | |
| 8,894,654 B2 | 11/2014 | Anderson | |
| 8,992,439 B2 | 3/2015 | Mulvihill et al. | |
| 9,220,483 B2 | 12/2015 | Frankhouser et al. | |
| 9,439,667 B2 | 9/2016 | Miller | |
| 9,451,968 B2 | 9/2016 | Miller | |
| 9,510,910 B2 | 12/2016 | Miller et al. | |
| 9,877,734 B2 | 1/2018 | Anderson | |
| 2002/0026126 A1 | 2/2002 | Burdorff et al. | |
| 2005/0222554 A1 | 10/2005 | Wallace et al. | |
| 2006/0095022 A1 | 5/2006 | Moll et al. | |
| 2007/0043338 A1 | 2/2007 | Moll et al. | |
| 2007/0197896 A1 | 8/2007 | Moll et al. | |
| 2010/0256558 A1 * | 10/2010 | Olson | A61B 34/77 |
| | | | 604/95.01 |
| 2013/0060278 A1 | 3/2013 | Bozung et al. | |
| 2014/0107471 A1 * | 4/2014 | Haider | A61B 5/1076 |
| | | | 606/82 |
| 2014/0262408 A1 | 9/2014 | Woodard | |
| 2014/0276839 A1 | 9/2014 | Forman et al. | |
| 2015/0073357 A1 | 3/2015 | Bagwell et al. | |
| 2015/0164486 A1 | 6/2015 | May et al. | |
| 2015/0208925 A1 | 7/2015 | Bagwell et al. | |
| 2015/0216557 A1 | 8/2015 | Mulvihill et al. | |
| 2015/0342618 A1 | 12/2015 | Nguyen | |
| 2016/0008026 A1 | 1/2016 | Elayaperumal et al. | |
| 2016/0175543 A1 | 6/2016 | Frankhouser et al. | |

* cited by examiner

BIOPSY DEVICE HAVING A LINEAR MOTOR

CROSS-REFERENCE TO RELATED APPLICATION

This application is a continuation of U.S. patent application Ser. No. 16/761,519, entitled "BIOPSY DEVICE HAVING A LINEAR MOTOR" and filed May 5, 2020, which is a U.S. national phase of International Application No. PCT/US/2017/067543, filed Dec. 20, 2017, each of which is incorporated herein by reference in its entirety.

TECHNICAL FIELD

The present invention relates to biopsy devices, and, more particularly, to a biopsy device having a linear motor.

BACKGROUND ART

In operating a typical handheld biopsy device, such as a bone biopsy device, it is up to the user to acquire a safe and accurate sample. Oftentimes, it is necessary for the user to apply a large force to the biopsy device in order to penetrate the tougher layers, such as the bone cortex, only to overshoot when breaking through and into the softer layers of bone and marrow. Also, sometimes the samples need to be taken near the lungs or other organs, and in such cases, an overshoot could cause excessive damage to the surrounding region, thus leading to procedural complications and lengthened recovery time.

What is needed in the art is a biopsy device that can perform the biopsy procedure with greater accuracy, so as to reduce the occurrence of overshoots during the biopsy procedure.

SUMMARY OF INVENTION

The present invention provides a biopsy device that can perform the biopsy procedure with greater accuracy, so as to reduce the occurrence of overshoots during the biopsy procedure, such as a bone biopsy procedure.

The invention in one form is directed to a biopsy device for driving a penetrating member. The biopsy device includes a device housing and a linear motor. The device housing has a handle portion configured to be grasped by a clinician's hand. The linear motor has a motor housing and a linear motor shaft. The motor housing is coupled to the device housing. The linear motor shaft is movable in the motor housing along a longitudinal axis. The linear motor shaft has a proximal end portion and a distal end portion having a distal end. The distal end portion is configured to be drivably coupled to the penetrating member. A controller circuit is operatively coupled to the linear motor. The controller circuit has a processor circuit, a first feedback circuit, and a second feedback circuit. The first feedback circuit has at least one drive characteristic sensor associated with the linear motor shaft. The second feedback circuit has a housing position detector connected to the device housing. The first feedback circuit and the second feedback circuit operate simultaneously. The processor circuit is configured to execute program instructions to control an axial advancement of the distal end of the linear motor shaft in accordance with a linear motor shaft advancement profile based on first control signals received from the at least one drive characteristic sensor of the first feedback circuit. Also, the processor circuit is configured to execute program instructions to keep the distal end of the linear motor shaft at a constant axial position consistent with the linear motor shaft advancement profile based on second control signals received from the housing position detector of the second feedback circuit so as to compensate for user movement of the device housing.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DESCRIPTION OF EMBODIMENTS

Figure 1:
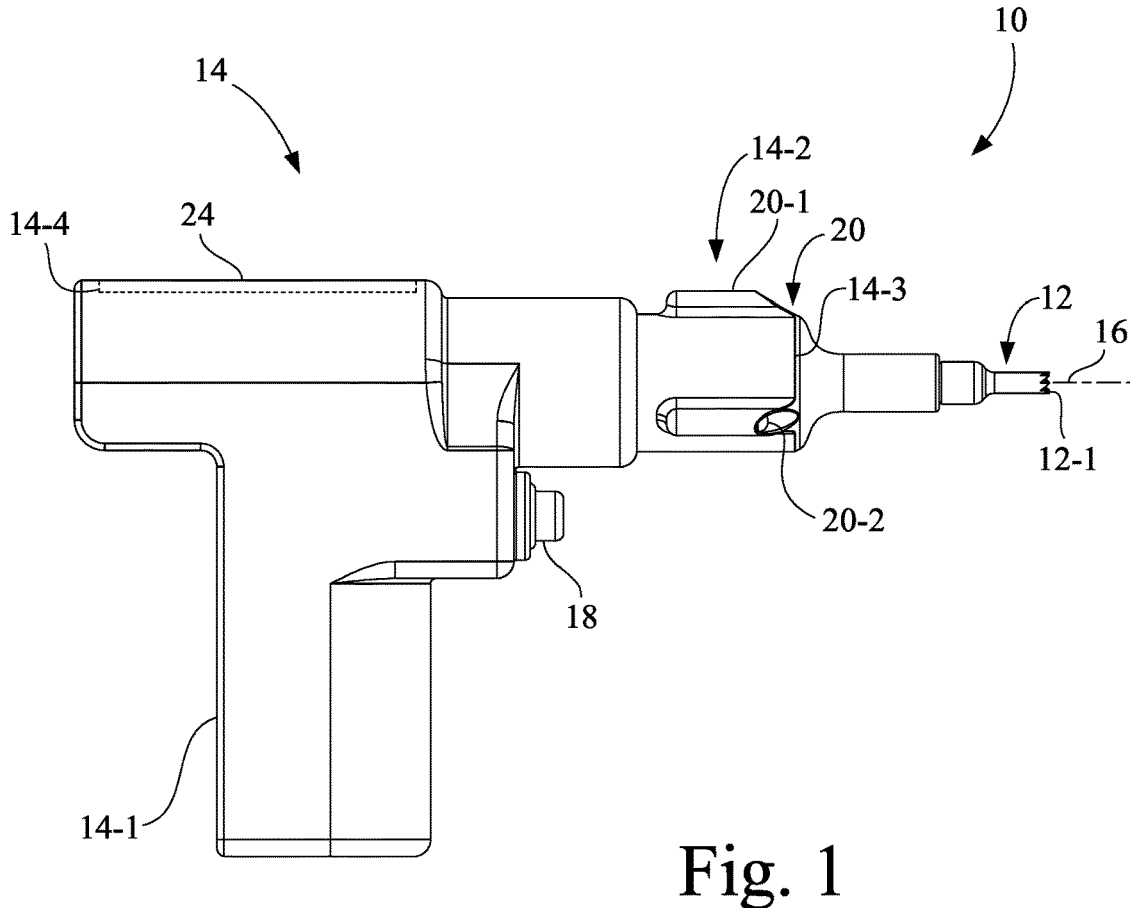
FIG. 1 is a side view of a biopsy device in accordance with an embodiment of the present invention.
Figure 2:
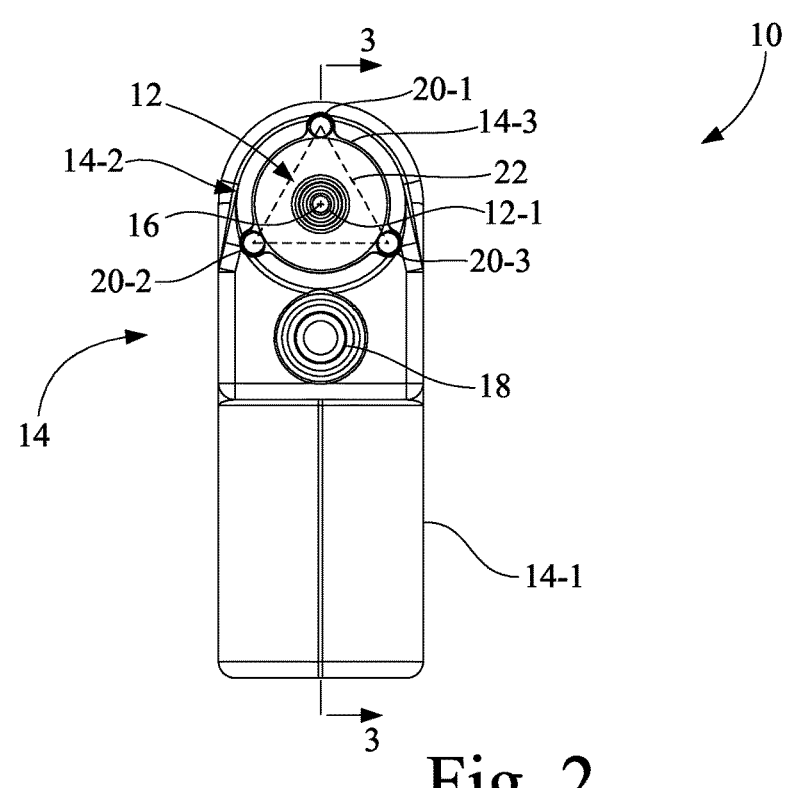
FIG. 2 is a front view of the biopsy device of FIG. 1.

Referring now to the drawings, and more particularly to FIGS. 1 and 2, there is shown a biopsy device 10 that is drivably coupled to a penetrating member 12 having a cutting tip 12-1. Penetrating member 12, for example, may be a metal (e.g., stainless steel) hollow shaft having cutting tip 12-1 as an annular arrangement of saw teeth.

Biopsy device 10 includes a device housing 14 having a handle portion 14-1 and a head portion 14-2. Handle portion 14-1 is configured to be grasped by a clinician's hand. Penetrating member 12 extends distally from head portion 14-2 of device housing 14 along a longitudinal axis 16. Movably coupled to device housing 14 is a trigger 18 for initiating movement of cutting tip 12-1. A housing position detector 20 is connected to device housing 14 so as to facilitate a determination of the position/orientation of device housing 14 of biopsy device 10 relative to the patient, and more particularly, relative to the entry point of cutting tip 12-1 of penetrating member 12 at a biopsy site of the patient.

In the present embodiment, housing position detector 20 is in the form of a plurality, e.g., three, position sensors 20-1, 20-2, and 20-3, mounted to head portion 14-2, and is exposed at a distal face 14-3 of head portion 14-2, of device housing 14 of biopsy device 10. The array of position sensors 20-1, 20-2, 20-3 may be configured using laser diode or acoustic (radar) distance sensors. Each of the position sensors 20-1, 20-2, and 20-3 is located at a respective vertex of a triangle 22, e.g., an equilateral triangle, and longitudinal axis 16 passes through triangle 22. More particularly, in the present embodiment, position sensors 20-1, 20-2, and 20-3 are spaced equally from one another at 120 degree increments around longitudinal axis 16, and are equidistant from longitudinal axis 16. Accordingly, housing position detector 20 may acquire linear distance measurements from each of position sensors 20-1, 20-2, 20-3, which in turn may be used to generate Cartesian coordinate information, and housing rotational orientation (vector) information, associated with device housing 14 relative to the patient.

Optionally, as shown by phantom lines in FIG. 1, device housing 14 may include a window 14-4 for exposing a user interface 24, which may be in the form of an LCD touch screen for receiving user inputs, and for displaying operation information.

Figure 3:
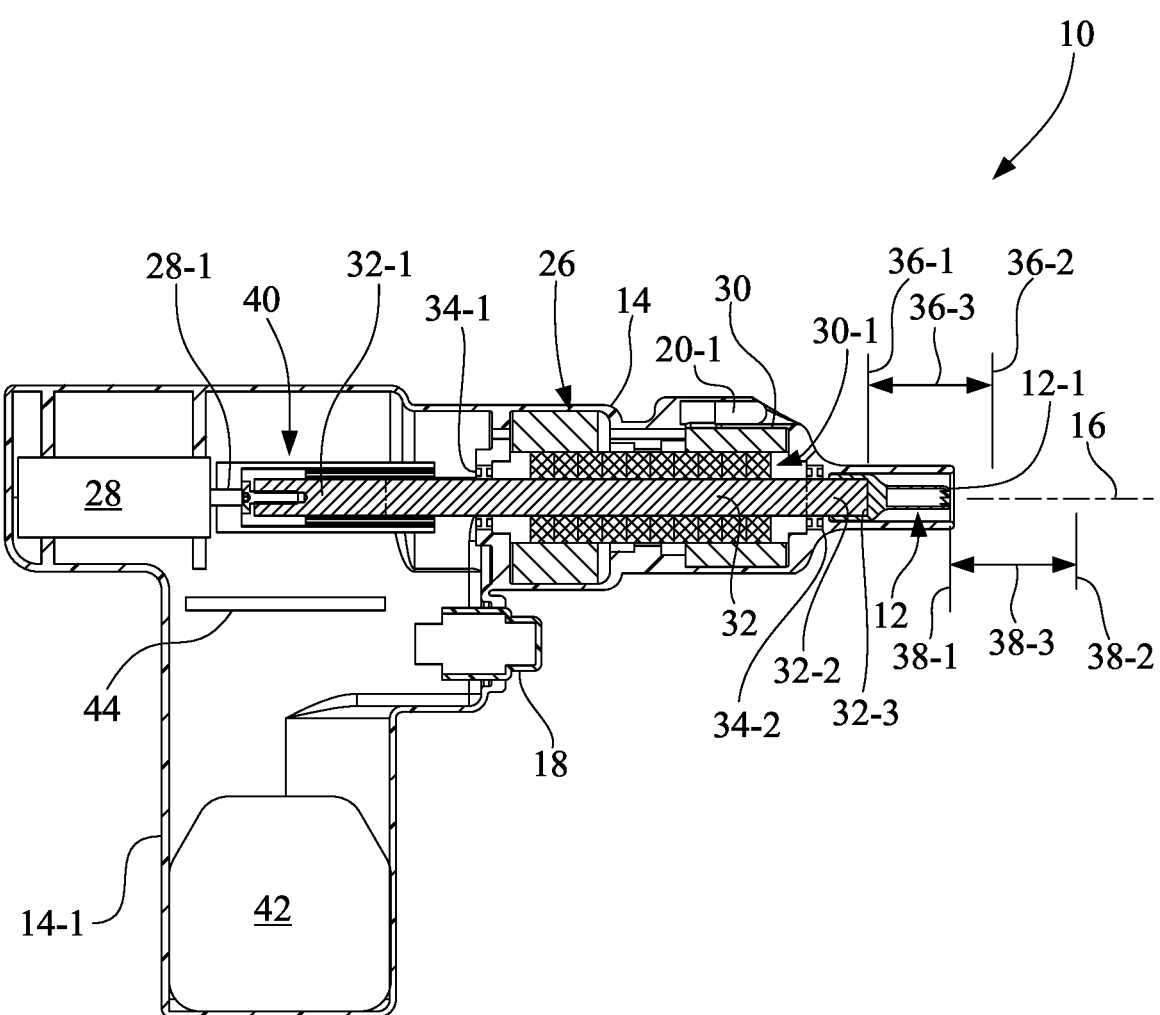
FIG. 3 is a section view of the biopsy device of FIGS. 1 and 2, take along line 3-3 of FIG. 2, and with the linear motor shaft and the penetrating member in a fully retracted position.
Figure 4:
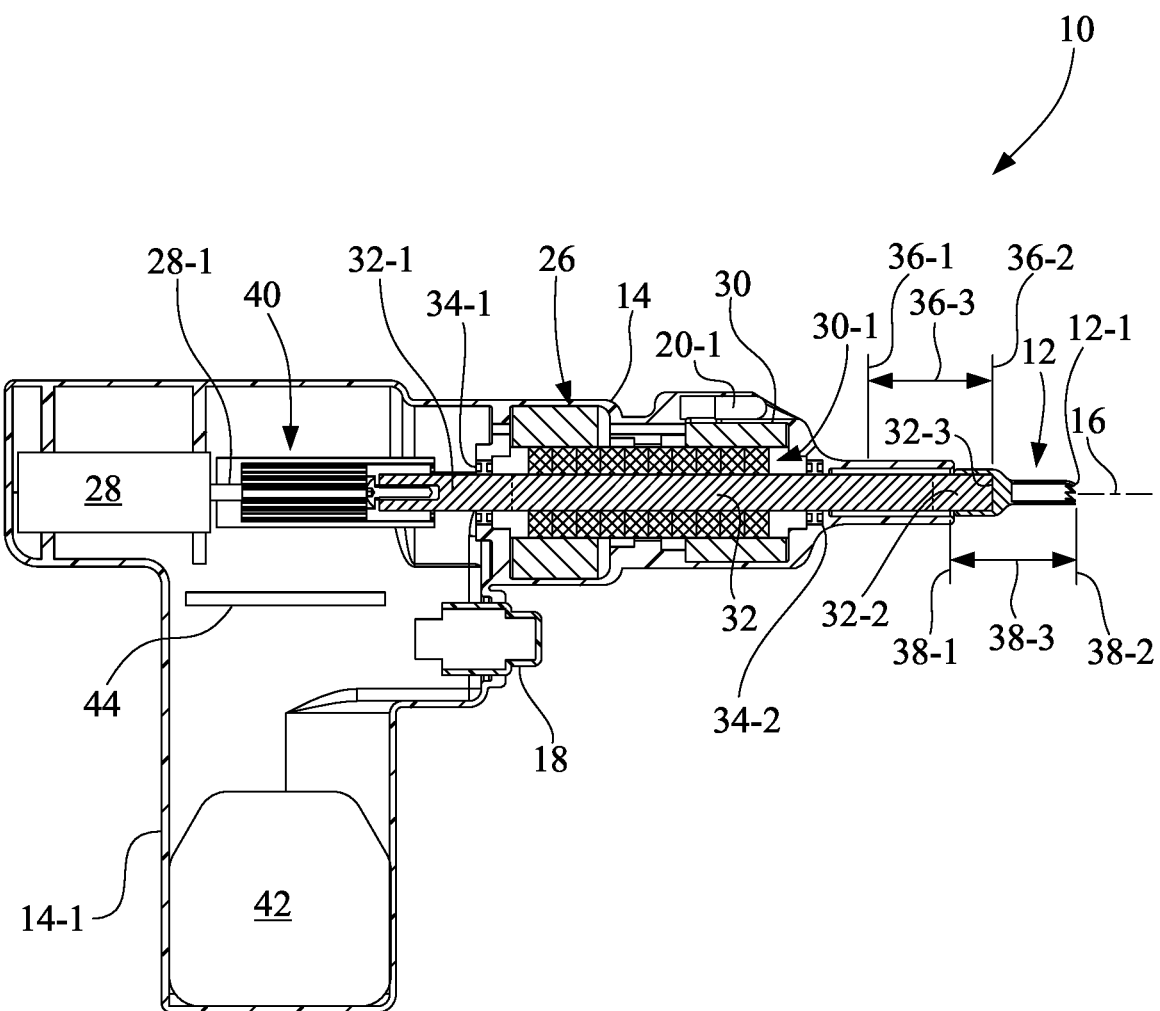
FIG. 4 is a section view of the biopsy device of FIGS. 1 and 2, take along line 3-3 of FIG. 2, and with the linear motor shaft and the penetrating member in a fully extended position.

Referring also to FIGS. 3 and 4, contained within device housing 14 is a linear motor 26 and a rotary motor 28.

In the present embodiment, linear motor 26 is an electrical linear motor that includes a motor housing 30 and a linear motor shaft 32. Motor housing 30 is mechanically coupled, e.g., fixedly attached, to device housing 14. Linear motor shaft 32 is axially movable in motor housing 30 along longitudinal axis 16.

Motor housing 30 may be formed around, or have mounted thereto, linear motor windings 30-1. Motor housing 30 further includes non-ferrous bushings 34-1, 34-2, or alternatively non-ferrous bearings, that are centered on longitudinal axis 16. Bushings 34-1, 34-2 are sized to slidably receive linear motor shaft 32, such that linear motor shaft 32 is axially movable in motor housing 30 along longitudinal axis 16. Linear motor shaft 32 has a proximal end portion 32-1, and a distal end portion 32-2 having a distal end 32-3. Distal end portion 32-2 is configured to be drivably coupled to penetrating member 12, e.g., by a hex drive, drill chuck, etc.

Referring to FIGS. 3 and 4, linear motor 26 is configured to axially move linear motor shaft 32 along longitudinal axis 16 in minute axial movements (e.g., 1-10 microns each) between a fully retracted position 36-1 and a fully extended position 36-2 throughout a maximum axial extent 36-3. When penetrating member 12 is drivably coupled to distal end portion 32-2 of linear motor shaft 32, cutting tip 12-1 is axially offset a fixed distance from distal end 32-3 of linear motor shaft 32, and penetrating member 12 and linear motor shaft 32 move in unison. Thus, cutting tip 12-1 is movable along with linear motor shaft 32 in corresponding minute axial movements (e.g., 1-10 microns each) between a fully retracted position 38-1 and a fully extended position 38-2 throughout a maximum axial extent 38-3.

Rotary motor 28 is interposed between device housing 14 and linear motor 26. Rotary motor 28 may be, for example, a direct current (DC) motor having a rotatable motor shaft 28-1 that is drivably coupled to proximal end portion 32-1 of linear motor shaft 32 of linear motor 26. Rotary motor 28 is configured to rotate linear motor shaft 32 about longitudinal axis 16. Linear motor shaft 32 of linear motor 26 is slidably mounted to rotatable motor shaft 28-1 via a linear coupler 40, which may be in the form of a linear guide gear tube, thereby facilitating axial movement of linear motor shaft 32 while transferring rotational motion to linear motor shaft 32.

Electrical power may be supplied to electrical components of biopsy device 10 by a battery 42 housed in handle portion 14-1 of device housing 14. Battery 42 may be, for example, a rechargeable lithium battery.

Also contained in device housing 14 is a controller circuit 44 that is operatively coupled to linear motor 26 and rotary motor 28.

Figure 5:
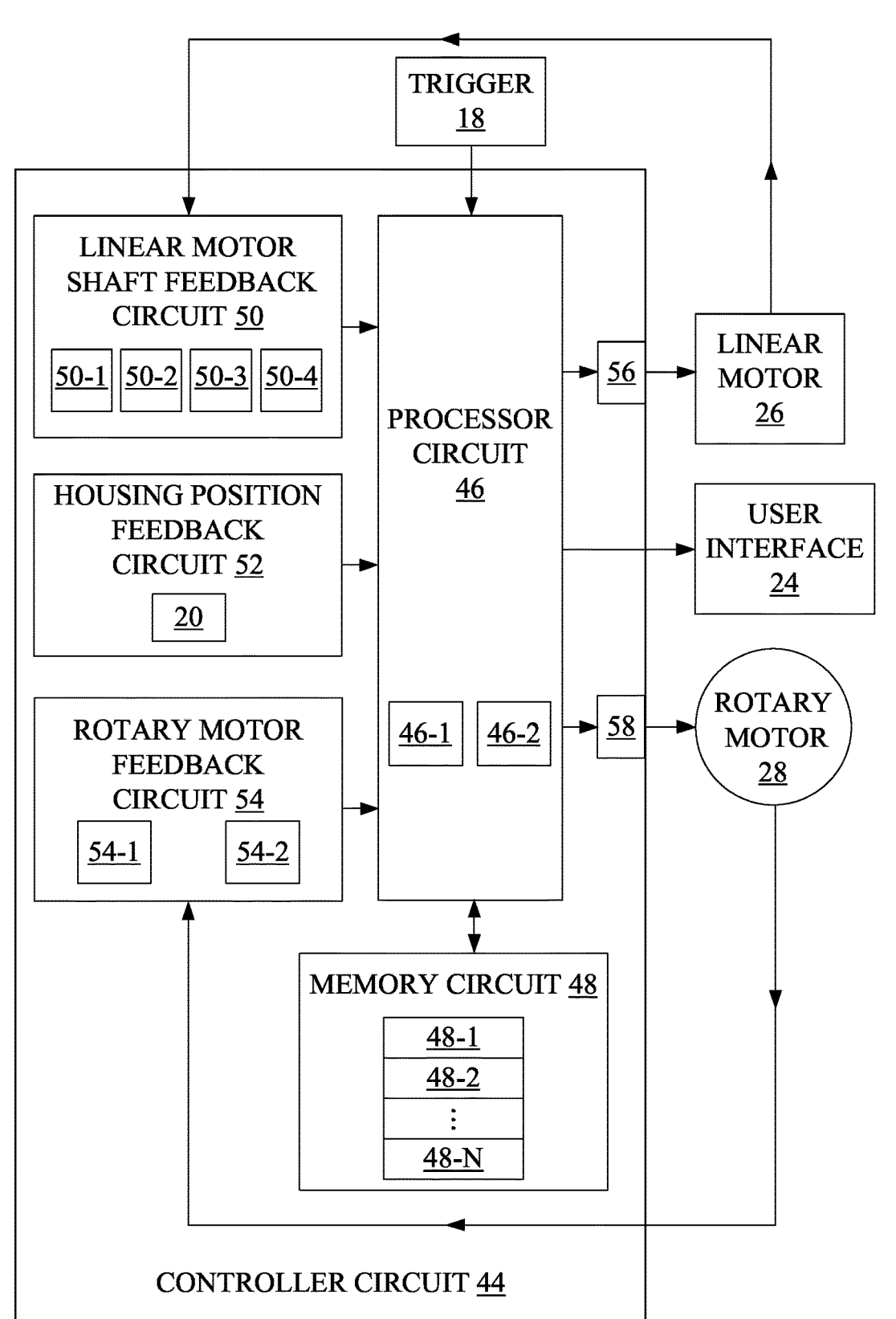
FIG. 5 is an electrical block diagram of a controller circuit of the biopsy device of FIG. 1.

Referring to FIG. 5, there is shown a block diagram of controller circuit 44. In the present embodiment, controller circuit 44 is operatively coupled, i.e., electrically and communicatively connected, to each of user interface 24, linear motor 26, and rotary motor 28, e.g., by wires and/or circuit traces. User interface 24 may be, for example, a touch input LCD display to aid the user in inputting control information, such as a linear motor shaft advancement profile for controlling the advancement of linear motor shaft 32, and also to display to user operational information, such as linear driving force, rotary driving speed (revolutions-per-minute (RPM)), and process duration (time) in relation to the advancement profile.

Controller circuit 44 includes a processor circuit 46, a memory circuit 48, a linear motor shaft feedback circuit 50, a housing position feedback circuit 52, a rotary motor feedback circuit 54, a linear motor driver circuit 56, and a rotary motor driver circuit 58. Controller circuit 44 may be formed as one or more Application Specific Integrated Circuits (ASIC).

Processor circuit 46 is electrically and communicatively connected to memory circuit 48, linear motor shaft feedback circuit 50, housing position feedback circuit 52, rotary motor feedback circuit 54, linear motor driver circuit 56, and rotary motor driver circuit 58, e.g., by wires and/or circuit traces.

Linear motor driver circuit 56 is electrically and communicatively connected to each of processor circuit 46 and linear motor 26. Linear motor driver circuit 56 receives linear motor drive signals from processor circuit 46, and conditions those signals for use in controlling the operation of linear motor 26. Linear motor driver circuit 56 may include, for example, one or more of a power amplifier circuit, a serial-to-parallel digital converter circuit, a parallel-to-serial digital converter circuit, a digital-to-analog converter circuit and/or a pulse width modulator circuit, depending upon the input signal requirements of linear motor 26.

Rotary motor driver circuit 58 is electrically and communicatively connected to each of processor circuit 46 and rotary motor 28. Rotary motor driver circuit 58 receives linear motor drive signals from processor circuit 46, and conditions those signals for use in controlling the operation of rotary motor 28. Rotary motor driver circuit 58 may include, for example, one or more of a power amplifier circuit, a serial-to-parallel digital converter circuit, a parallel-to-serial digital converter circuit, a digital-to-analog converter circuit and/or a pulse width modulator circuit, depending upon the input signal requirements of rotary motor 28.

Processor circuit 46 includes, for example, a microprocessor 46-1, a non-transitory electronic memory circuit 46-2, and associated circuitry, such as an input/output interface, clock, buffers, etc. Memory circuit 46-2 is non-transitory electronic memory, and may include volatile memory, such as random access memory (RAM), and/or non-volatile memory, such as read only memory (ROM), electronically erasable programmable ROM (EEPROM), NOR flash memory, NAND flash memory, etc.

Memory circuit 48 is non-transitory electronic memory, and may include volatile memory, such as random access memory (RAM), and/or non-volatile memory, such as read only memory (ROM), electronically erasable programmable ROM (EEPROM), NOR flash memory, NAND flash memory, etc. Memory circuit 48 is used to store operational information associated with linear motor 26 and/or rotary motor 28.

Stored in memory circuit 48 is one or more linear motor shaft advancement profiles 48-1, 48-2, . . . 48-N, associated with linear motor shaft 32, and in turn, associated with the penetrating member, e.g., penetrating member 12, that is drivably connected to linear motor shaft 32. For example, linear motor shaft advancement profile 48-1 may be a constant rate profile (steady state) associated with bone penetration; linear motor shaft advancement profile 48-2 may be a constant rate profile (steady state) associated with soft tissue penetration; etc. The "rate" may be units of distance, e.g., millimeters (mm), versus time in seconds, e.g., a linear motor shaft advancement rate of 1.0 mm/second at steady state.

It is contemplated that one or more of the linear motor shaft advancement profiles 48-1, 48-2, . . . 48-N may include a startup acceleration ramp having a ramp-up rate starting at time zero to a time of the start of the constant rate at steady state. It is also contemplated that one or more of the linear motor shaft advancement profiles 48-1, 48-2, . . . 48-N may include a deceleration ramp at the end of the constant rate at steady state, or alternatively, an abrupt shutoff at the end of the constant rate at steady state. It is further contemplated that one or more of the linear motor shaft advancement profiles 48-1, 48-2, . . . 48-N may include non-linear acceleration and/or non-linear (non-constant rate) steady state linear motor shaft advancement profile portions, if desired.

Linear motor shaft feedback circuit 50 includes at least one drive characteristic sensor, and in the present embodiment, includes a plurality of sensors to monitor conditions relating to linear motor shaft 32. In particular, linear motor shaft feedback circuit 50 may include an axial force sensor 50-1, an axial position sensor array 50-2, a time sensor 50-3, e.g., clock, and a temperature sensor 50-4. Axial force sensor 50-1 may be, for example, an electrical strain gauge located on or in linear motor shaft 32. Axial position sensor array 50-2 may include a plurality of optical sensors, or a plurality of Hall-effect sensors, configured to provide measurement of incremental (e.g., micron) distances of axial movement of linear motor shaft 32 during each of extension or retraction of linear motor shaft 32. Time sensor 50-3 is configured to provide time feedback for use by processor circuit 46 in calculating an actual rate of axial movement of linear motor shaft 32. Optionally, a temperature sensor 50-4 may provide temperature feedback associated with distal end portion 32-2 of linear motor shaft 32 and penetrating member 12.

Axial force sensor 50-1, axial position sensor array 50-2, and time sensor 50-3 of linear motor shaft feedback circuit 50 are used by processor circuit 46 to establish a position of distal end 32-3 of linear motor shaft 32 in accordance with a selected one of linear motor shaft advancement profiles 48-1, 48-2, . . . 48-N. Moreover, linear motor shaft feedback circuit 50 is used by processor circuit 46 to control an axial advancement of distal end 32-3 of linear motor shaft 32 in accordance with a selected one of linear motor shaft advancement profiles 48-1, 48-2, . . . 48-N based on control signals received from the drive characteristic sensor(s), e.g., axial force sensor 50-1, axial position sensor array 50-2, and time sensor 50-3, of linear motor shaft feedback circuit 50. In other words, the feedback loop provided by linear motor shaft feedback circuit 50 is used by processor circuit 46 to establish the cutting/coring of cutting tip 12-1 of penetrating member 12 through the biopsy site at a determined depth and advancement at a determined rate as determined by a comparison of the measured position of linear motor shaft 32 to the selected one of linear motor shaft advancement profiles 48-1, 48-2, . . . 48-N. Optionally, linear motor 26 may linearly oscillate, in addition to distally progressing, linear motor shaft 32, and in turn cutting tip 12-1 of penetrating member 12, in order to offer a chisel cut behavior through the various layers of the tissue, e.g., bone.

The feedback loop provided by linear motor shaft feedback circuit 50 may use the axial force, axial position, and temperature feedback associated with linear motor shaft 32 to control the amplitude and frequency of the chiseling and progression of linear motor shaft 32; faster cycling with less amplitude for harder material, slower cycling and more amplitude for softer material.

Housing position feedback circuit 52 includes housing position detector 20 having the triangular arrangement of position sensors 20-1, 20-2, 20-3, as described above. The feedback loop provided by housing position feedback circuit 52 is used to keep the depth of distal end 32-3 of linear motor shaft 32, and in turn the depth of cutting tip 12-1 of penetrating member 12, at a constant axial position, e.g., zero position, relative to device housing 14 of biopsy device 10, as offset by the position at a particular time as indicated by the selected one of linear motor shaft advancement profiles 48-1, 48-2, . . . 48-N. More particularly, processor circuit 46 is configured to execute program instructions to keep distal end 32-3 of linear motor shaft 32, and in turn the cutting tip 12-1 of penetrating member 12, at a constant axial position, e.g., zero position, as offset by the position at a particular time indicated by the selected one of linear motor shaft advancement profiles 48-1, 48-2, . . . 48-N, based on second control signals received from housing position detector 20 of housing position feedback circuit 52 so as to compensate for user movement of device housing 14 of biopsy device 10.

The array of position sensors 20-1, 20-2, 20-3 may be configured as a laser or acoustic (radar) distance meter that provide distance measurement signals to processor circuit 46. Processor circuit 46 executes program instructions to process the distance measurement signals and to generate motor control signals that are sent to linear motor driver circuit 56. Linear motor driver circuit 56 conditions the motor control signals, as appropriate, and supplies corresponding drive signals to linear motor 26 to adjust the position of linear motor shaft 32, and in turn the position of cutting tip 12-1 of penetrating member 12 relative to the position of device housing 14 of biopsy device 10, and in turn, the patient.

Considering housing position feedback circuit 52 by itself, i.e., without utilizing the linear motor shaft advancement profile for linear motor 26, upon beginning of the biopsy drilling operation by actuating trigger 18, cutting tip 12-1 of penetrating member 12 would be dynamically moved to maintain a particular location, e.g., zero position, as biopsy device 10 is moved toward or away from the patient. This aspect compensates for the shifting of the posture of the user, or other movement of the user. Thus, housing position feedback circuit 52 operates to prevent cutting tip 12-1 of penetrating member 12 from being at an undetermined location requiring a restart of the procedure or another scan.

Rotary motor feedback circuit 54 is optionally provided to provide additional feedback information to processor circuit 46 relating to the rotational speed (RPM) of linear motor shaft 32 and/or the rotational force (torque) applied to linear motor shaft 32 as a result of operating rotary motor 28. Rotary motor feedback circuit 54 is considered as an optional feedback loop, and as such, it is contemplated that the present invention may be implemented with, or without, the feedback loop established by rotary motor feedback circuit 54. Rotary motor feedback circuit 54 may include at least one of a torque sensor 54-1 and a rotational speed feedback sensor 54-2 to monitor a rotary force applied to linear motor shaft 32 by rotary motor 28.

In one implementation, for example, torque may be determined by monitoring the current required by rotary motor 28, and the rotational speed (RPM) may be measured using an encoder wheel/optical sensor arrangement. Optionally, the torque and rotational speed may be measured using sensors located in linear coupler 40, e.g., a gear box. By utilizing this optional third feedback loop established by rotary motor feedback circuit 54, however, both of linear motor 26 and rotary motor 28 may be stopped immediately after a large drop in torque and/or high increase in rpm occurs, such as, for example, when cutting tip 12-1 of penetrating member 12 passes through the bone cortex.

Processor circuit 46 is configured to execute program instructions to axially advance the distal end 32-3 of linear motor shaft 32 in accordance with a selected one of linear motor shaft advancement profiles 48-1, 48-2, . . . 48-N. The selection of one of the linear motor shaft advancement profiles 48-1, 48-2, . . . 48-N is made by the user prior to beginning the biopsy procedure by providing a user input at user interface 24, and upon making the selection, the selected one of linear motor shaft advancement profiles 48-1, 48-2, . . . 48-N is retrieved from memory circuit 48 and loaded into memory circuit 46-2 of processor circuit 46 for use during the biopsy procedure.

Processor circuit 46 is configured via software and/or firmware residing in memory circuit 46-2 to execute program instructions to monitor linear motor shaft feedback circuit 50, housing position feedback circuit 52, and rotary motor feedback circuit 54, and in turn to generate linear motor control signals supplied to linear motor driver circuit 56 and to generate rotary motor control signals that are supplied to rotary motor driver circuit 58, so as to control the axial position of linear motor shaft 32 relative to device housing 14 in accordance with the selected one of linear motor shaft advancement profiles 48-1, 48-2, . . . 48-N, and to generate rotary motor control signals that are supplied to rotary motor driver circuit 58.

In particular, in accordance with linear motor shaft feedback provided by linear motor shaft feedback circuit 50, processor circuit 46 compares an actual rate of linear motor shaft advancement derived from inputs from linear motor shaft feedback circuit 50 to the selected one of linear motor shaft advancement profiles 48-1, 48-2, . . . 48-N stored in memory circuit 48 for making dynamic adjustments to the linear motor control signals supplied to linear motor driver circuit 56.

Also, in accordance with the housing position feedback provided by housing position feedback circuit 52, the "zero" axial position of linear motor shaft 32 relative to the target (e.g., bone surface) is maintained during operation by adjusting the axial position of linear motor shaft 32 relative to device housing 14 during the biopsy procedure so as to abide by the selected one of the linear motor shaft advancement profiles 48-1, 48-2, . . . 48-N. As such, the invention is able to compensate for small changes in position of the user and/or the patient during the biopsy procedure, as well as to compensate for variations in the force applied by the user to device housing 14 during the biopsy procedure, which otherwise may result in an advancement of cutting tip 12-1 of penetrating member 12 into the target tissue at a rate that is not consistent with the rate defined by the selected one of the linear motor shaft advancement profiles 48-1, 48-2, . . . 48-N.

A biopsy procedure is performed by biopsy device 10 by first positioning biopsy device 10 at an initial position relative to the patent, and then activating trigger 18. Upon activation of trigger 18, all of the feedback loops are initialized, and housing position feedback circuit 52 establishes the zero position of linear motor shaft 32 and cutting tip 12-1 of penetrating member 12 relative to device housing 14. Processor circuit 46 then controls rotary motor 28 to begin rotation of linear motor shaft 32, and controls linear motor 26 to axially advance liner motor shaft 32, and in turn cutting tip 12-1 of penetrating member 12, in accordance with a selected one of the linear motor shaft advancement profiles 48-1, 48-2, . . . 48-N.

In accordance with an aspect of the invention, the feedback loops run simultaneously, i.e., in parallel. Thus, in the present embodiment, the feedback loop established by linear motor shaft feedback circuit 50, the feedback loop established by housing position feedback circuit 52, and optionally the feedback loop established by rotary motor feedback circuit 54, run simultaneously, i.e., in parallel. Since these feedback loops are run in parallel, the user can either hold steady or constantly adjust the location/orientation of biopsy device 10 relative to the patient, and cutting tip 12-1 of penetrating member 12 will still advance through the tissue (e.g., by drilling and/or chiseling) at the biopsy site at the predefined rate defined by the selected one of the linear motor shaft advancement profiles 48-1, 48-2, . . . 48-N, and optionally control rotation of linear motor shaft 32 by rotary motor 28 in accordance with a specified torque (also stored in and retrieved from memory circuit 48) that may be associated with a given tissue toughness/density.

Processor circuit 46 may execute program instructions to perform the equation: depth=initial distance−current distance+sample advancement distance, wherein the "sample advancement distance" is determined at a particular time in the advancement curve defined by the selected one of the linear motor shaft advancement profiles 48-1, 48-2, . . . 48-N, so as to keep cutting tip 12-1 of penetrating member 12 at a known location over time. The optional rotary motor feedback circuit 54 may monitor the RPM and torque applied to linear motor shaft 32.

In accordance with the operation of the present invention, linear motor 26 may react in real-time to many situations that may occur during a biopsy procedure, such as for example:

1. If the user moves biopsy device 10 closer to the patient than expected, linear motor shaft 32, and in turn cutting tip 12-1 of penetrating member 12, will be retracted by that same amount while still advancing linear motor shaft 32 in accordance with the drilling routine defined by the selected one of the linear motor shaft advancement profiles 48-1, 48-2, . . . 48-N, and also may compensate the torque and rotational speed as necessary.

2. If the user moves biopsy device 10 further from the patient than expected, then linear motor shaft 32, and in turn cutting tip 12-1 of penetrating member 12, will be extended by that same amount while still advancing linear motor shaft 32 in accordance with the drilling routine defined by the selected one of the linear motor shaft advancement profiles 48-1, 48-2, . . . 48-N, and may also compensate the torque and rotational speed as necessary.

3. In a bone biopsy, if the user drills through the outer hard layers of the bone and a large torque drop combined with an RPM increase is detected by rotary motor feedback circuit 54, biopsy device 10 may immediately stop drilling and retract linear motor shaft 32 and cutting tip 12-1 into biopsy device 10, leaving only the blunt end of device housing 14 exposed to the patient (see FIG. 3), so as to avoid secondary sticks and discomfort of the patient.

The following items also relate to the invention:

In one form, the invention relates to a biopsy device for driving a penetrating member. The biopsy device includes a device housing and a linear motor. The device housing has a handle portion configured to be grasped by a user's hand. The linear motor has a motor housing and a linear motor shaft. The motor housing is coupled to the device housing. The linear motor shaft is movable in the motor housing along a longitudinal axis. The linear motor shaft has a proximal end portion and a distal end portion having a distal end. The distal end portion is configured to be drivably coupled to the penetrating member. A controller circuit is operatively coupled to the linear motor. The controller circuit has a processor circuit, a first feedback circuit, and a second feedback circuit. The first feedback circuit has at least one drive characteristic sensor associated with the linear motor shaft. The second feedback circuit has a housing position detector connected to the device housing. The controller circuit is configured to operate the first feedback circuit and the second feedback circuit simultaneously. The processor circuit is configured to execute program instructions to control an axial advancement of the distal end of the linear motor shaft in accordance with a linear motor shaft advancement profile based on first control signals received from the at least one drive characteristic sensor of the first feedback circuit. Also, the processor circuit is configured to execute program instructions to keep the distal end of the linear motor shaft at a constant axial position, as offset by the position indicated by the linear motor shaft advancement profile, based on second control signals received from the housing position detector of the second feedback circuit so as to compensate for user movement of the device housing.

The at least one drive characteristic sensor may be configured to provide one or more of force feedback, position feedback, and temperature feedback.

Optionally, the biopsy device may include a rotary motor interposed between the device housing and the linear motor. The rotary motor has a rotatable motor shaft that may be drivably coupled to the proximal end portion of the linear motor shaft of the linear motor and may be configured to rotate the linear motor shaft about the longitudinal axis.

Optionally, the biopsy device may include a third feedback circuit having at least one of a torque sensor and a rotational speed sensor to monitor a rotary force applied to the linear motor shaft by the rotary motor.

The biopsy device may include a penetrating member connected to the distal end portion of the linear motor shaft, the penetrating member having a cutting tip.

Optionally, the controller circuit may be configured to operate the linear motor to generate a linear oscillation of the linear motor shaft, and in turn, a linear oscillation of the cutting tip of the penetrating member.

The controller circuit may be configured to operate the linear motor and the rotary motor to generate both a linear oscillation and a rotary motion of the cutting tip of the penetrating member.

The housing position detector may include three position sensors mounted at a head portion of the device housing. Each position sensor of the three position sensors may be located at a respective vertex of a triangle, and the longitudinal axis of the linear motor shaft passes through the triangle.

The biopsy device may include a memory circuit that is electrically and communicatively connected to the processor circuit. The linear motor shaft advancement profile referenced above may be a selected one of a plurality of linear motor shaft advancement profiles stored in the memory circuit.

The linear motor shaft advancement profile may be a constant rate profile.

The at least one drive characteristic sensor of the first feedback circuit may include an axial force sensor, an axial position sensor array, and/or a temperature sensor, associated with the linear motor shaft.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device for driving a penetrating member, comprising:
   a controller circuit having a processor circuit, a first feedback circuit, and a second feedback circuit, the first feedback circuit having at least one drive characteristic sensor associated with a linear motor shaft of a linear motor and the second feedback circuit having a housing position detector connected to a device housing, the first feedback circuit and the second feedback circuit operating simultaneously, wherein:
   the processor circuit is configured to execute program instructions to control an axial advancement of a distal end of the linear motor shaft in accordance with a linear motor shaft advancement profile based on first control signals received from the at least one drive characteristic sensor of the first feedback circuit, and
   the processor circuit is further configured to execute program instructions to keep the distal end of the linear motor shaft at a constant axial position, as offset by a position indicated by the linear motor shaft advancement profile, based on second control signals received from the housing position detector of the second feedback circuit so as to compensate for user movement of the device housing.

2. The biopsy device of claim 1, wherein the at least one drive characteristic sensor is configured to provide force feedback, position feedback, and temperature feedback.

3. The biopsy device of claim 1, further comprising a third feedback circuit having at least one of a torque sensor and a rotational speed sensor to monitor a rotary force applied to the linear motor shaft by a rotary motor interposed between the device housing and the linear motor.

4. The biopsy device of claim 1, wherein the controller circuit is further configured to operate the linear motor to generate a linear oscillation of a cutting tip of the penetrating member.

5. The biopsy device of claim 1, wherein the controller circuit is further configured to operate the linear motor and a rotary motor to generate both a linear oscillation and a rotary motion of a cutting tip of the penetrating member.

6. The biopsy device of claim 1, wherein the housing position detector comprises three position sensors mounted at a head portion of the device housing, each position sensor of the three position sensors being located at a respective vertex of a triangle, and the longitudinal axis of the linear motor shaft passes through the triangle.

7. The biopsy device of claim 6, wherein the three position sensors are equidistant from the longitudinal axis.

8. The biopsy device of claim 1, further comprising a memory circuit that is electrically and communicatively connected to the processor circuit, and wherein the linear motor shaft advancement profile is a selected one of a plurality of linear motor shaft advancement profiles stored in the memory circuit.

9. The biopsy device of claim 1, wherein the linear motor shaft advancement profile is a constant rate profile.

10. The biopsy device of claim 1, wherein the at least one drive characteristic sensor of the first feedback circuit includes an axial force sensor, an axial position sensor array, and a temperature sensor that are associated with the linear motor shaft.

11. A controller circuit, comprising:

a first feedback circuit having at least one drive characteristic sensor associated with a linear motor shaft of a linear motor;

a second feedback circuit having a housing position detector connected to a device housing;

a processor circuit communicatively coupled to the first feedback circuit and the second feedback circuit; and non-transitory, processor readable memory circuit communicatively coupled to the processor circuit, the non-transitory, processor readable memory circuit comprising programming instructions thereon that, when executed by the processor circuit, cause the processor circuit to:

control an axial advancement of a distal end of the linear motor shaft in accordance with a linear motor shaft advancement profile based on first control signals received from the at least one drive characteristic sensor of the first feedback circuit, and maintain the distal end of the linear motor shaft at a constant axial position, as offset by a position indicated by the linear motor shaft advancement profile, based on second control signals received from the housing position detector of the second feedback circuit so as to compensate for user movement of the device housing.

12. The controller circuit of claim 11, wherein the at least one drive characteristic sensor is configured to provide force feedback, position feedback, and temperature feedback.

13. The controller circuit of claim 11, further comprising a third feedback circuit having at least one of a torque sensor and a rotational speed sensor to monitor a rotary force applied to the linear motor shaft by a rotary motor interposed between the device housing and the linear motor.

14. The controller circuit of claim 11, wherein the programming instructions further cause the processor circuit to operate the linear motor to generate a linear oscillation of a cutting tip of a penetrating member.

15. The controller circuit of claim 11, wherein the programming instructions further cause the processor circuit to operate the linear motor and a rotary motor to generate both a linear oscillation and a rotary motion of a cutting tip of a penetrating member.

16. The controller circuit of claim 11, wherein the housing position detector comprises three position sensors mounted at a head portion of the device housing, each position sensor of the three position sensors being located at a respective vertex of a triangle, and the longitudinal axis of the linear motor shaft passes through the triangle.

17. The controller circuit of claim 16, wherein the three position sensors are equidistant from the longitudinal axis.

18. The controller circuit of claim 11, wherein the linear motor shaft advancement profile is a selected one of a plurality of linear motor shaft advancement profiles stored in the non-transitory, processor readable memory circuit.

19. The controller circuit of claim 11, wherein the linear motor shaft advancement profile is a constant rate profile.

20. The controller circuit of claim 11, wherein the at least one drive characteristic sensor of the first feedback circuit includes an axial force sensor, an axial position sensor array, and a temperature sensor that are associated with the linear motor shaft.

\* \* \* \* \*